US012669721B2

(12) United States Patent
Chou et al.

(10) Patent No.: US 12,669,721 B2
(45) Date of Patent: Jun. 30, 2026

(54) FUNCTIONAL PATCH FOR USE WITH CONTACT LENS

(71) Applicant: OPENVISION CORPORATION, Taoyuan City (TW)

(72) Inventors: Ming-Yi Chou, Taoyuan County (TW); Ta-Jen Hsing, Taipei City (TW); Sung-Yuan Chiang, Taipei City (TW); Takahiro Takahashi, Taoyuan City (TW)

(73) Assignee: OPENVISION CORPORATION, Taoyuan City (TW)

( * ) Notice: Subject to any disclaimer, the term of this patent is extended or adjusted under 35 U.S.C. 154(b) by 220 days.

(21) Appl. No.: 18/766,923

(22) Filed: Jul. 9, 2024

(65) Prior Publication Data

US 2025/0085570 A1       Mar. 13, 2025

(30) Foreign Application Priority Data

Sep. 13, 2023    (TW) ................................. 112134965

(51) Int. Cl.
| | |
|---|---|
| *G02C 7/04* | (2006.01) |
| *A61B 5/00* | (2006.01) |
| *G02B 1/04* | (2006.01) |
| *G02C 7/10* | (2006.01) |

(52) U.S. Cl.
CPC ............ *G02C 7/049* (2013.01); *A61B 5/4866* (2013.01); *G02B 1/043* (2013.01); *G02C 7/046* (2013.01); *G02C 7/108* (2013.01); *G02C 2202/16* (2013.01); *G02C 2202/18* (2013.01)

(58) Field of Classification Search
CPC ........ G02C 7/049; G02C 7/108; G02C 7/104; G02C 7/046; G02C 2202/18
USPC .............. 351/159.02, 159.24, 159.29, 159.3, 351/159.32, 159.33
See application file for complete search history.

(56) References Cited

U.S. PATENT DOCUMENTS

| | | | | | |
|---|---|---|---|---|---|
| 4,121,885 | A | * | 10/1978 | Erickson ................ | G02C 7/049 264/1.7 |
| 6,467,904 | B1 | * | 10/2002 | Gartley ............ | B29D 11/00038 264/1.36 |
| 2015/0234204 | A1 | * | 8/2015 | Havenstrite ............ | G02B 1/043 351/159.33 |

(Continued)

*Primary Examiner* — Wyatt A Stoffa
*Assistant Examiner* — Seth D Moser
(74) *Attorney, Agent, or Firm* — Rabin & Berdo, P.C.

(57) ABSTRACT

A functional patch for use with a contact lens includes an attaching layer and a functional patterned layer. The contact lens and the attaching layer are made of different hydrophilic materials to present two net-like structures respectively contain a plurality of first pores and second pores, and the second pores have pore size smaller than that of the first pores. The attaching layer is adsorbable to and detachable from the contact lens. A part of the functional patterned layer permeates into the second pores and the remaining part of the functional patterned layer is cured on the surface of the attaching layer. The attaching layer has closely arranged molecular chain blocks to form net-like structure having relatively small pore size. Therefore, only a limited amount of the material molecules of the functional patterned layer is permeated into the second pores, allowing the functional patterned layer to have a smooth surface.

9 Claims, 13 Drawing Sheets

(56) References Cited

U.S. PATENT DOCUMENTS

| | | | | |
|---|---|---|---|---|
| 2016/0041407 | A1* | 2/2016 | Chou ..................... | G02C 11/02 |
| | | | | 351/159.24 |
| 2016/0341977 | A9* | 11/2016 | Burton ................... | G02C 7/102 |
| 2021/0132409 | A1* | 5/2021 | Hackett ................... | G02C 7/04 |
| 2022/0197056 | A1* | 6/2022 | Tucker ................... | G02C 11/10 |

* cited by examiner

FUNCTIONAL PATCH FOR USE WITH CONTACT LENS

FIELD OF THE INVENTION

The present invention relates to a functional patch for use with a contact lens, and more particularly, to a functional patch that provides the contact lens with additional functions without influencing the original eyesight correction function of the contact lens.

BACKGROUND OF THE INVENTION

Contact lenses are thin lenses for resting on the surface of a user's eyes to correct or protect the user's eyesight. Without the conventional thick and heavy eye glasses frame and lenses, the contact lenses have the advantages of small in volume, conveniently portable, having no reverse influence on the user's appearance, and feeling free from any weight or pressure. Therefore, since the contact lenses were introduced into the market, they have been widely welcomed by the public, particularly by the young people and people who care about their beauty and appearance.

With changes in times and maturation in technology, the current contact lenses are used not only to correct the user's eyesight, but also used to modify the color of the user's iris or enlarge the user's eyes. Furthermore, microelectronic devices can be embedded in the contact lenses to detect the basal metabolic rate values in the user's tear, so as to have an idea about the blood sugar levels in the user's body.

In the currently commercially available contact lenses, since the colored pattern is provided inside the lenses, the user has to purchase two or more pairs of contact lenses with differently colored patterns if the user wants to change the color or pattern of the contact lenses. It is of course inconvenient and uneconomical to do so. Besides, as shown in FIG. 1, the currently available colored contact lens 3 is formed by pad printing or jet printing an ink patterned layer 31 onto the surface of a lens layer 32 made of a hydrophilic material. Since the lens layer 32 is formed of a hydrophilic material that presents a net-like structure containing a plurality of pores 321, a large part of the ink forming the patterned layer 31 would permeate into the pores 321 on the lens layer 32 before the patterned layer 31 and the lens layer 32 are cured. As a result, the cured patterned layer 31 and the lens layer 32 would have an uneven surface. As to the present contact lenses with microelectronic devices, the microelectronic devices are directly embedded in the contact lenses in the manufacturing process. Since it is very difficult to set the microelectronic device on the spherical surface of the contact lens, there are more limits in use and fewer choices in lens diopters in terms of the contact lenses with microelectronic devices. When the user has changes in his or her positive or negative diopters, he or she has to purchase another pair of contact lenses with microelectronic devices with matching diopters. This is of course very inconvenient for the user to do so.

Further, in the case the commercially available colored contact lenses or contact lenses with microelectronic devices also provide the function of eyesight correction, the contact lenses will be much more expensive than common contact lenses and inevitably lower the user's willingness to purchase the contact lenses.

SUMMARY OF THE INVENTION

A primary object of the present invention is to provide a functional patch providing the contact lens with additional functions. The functional patch includes an attaching layer, of which the molecular chain blocks are relatively closely arranged to form a net-like structure having relatively small pore size, giving the attaching layer a structural pattern different from that of a common contact lens. The functional patch further has a functional patterned layer form on the surface of the attaching layer. A very limited part of the material molecules of the functional patterned layer is permeated into the attaching layer, such that the cured functional patterned layer has a relatively smooth surface without unevenness or damage.

To achieve the above and other objects, the functional patch for use with a contact lens according to the present invention includes an attaching layer and a third hydrophilic material. The contact lens is formed of a first hydrophilic material to present a first net-like structure containing a plurality of first pores.

The attaching layer is formed of a second hydrophilic material, which is different from the first hydrophilic material, to present a second net-like structure. The attaching layer presenting the second net-like structure form an attaching surface adsorbable to the contact lens, a plurality of discontinuous connecting surfaces spaced on along the attaching surface, and a plurality of second pores located between the attaching surface and the connecting surfaces. The second pores have pore size smaller than that of the first pores.

The third hydrophilic material is provided on the connecting surfaces to form a functional patterned layer, which includes permeated portions that permeate into the second pores, and exposed portions located on an outer side of the connecting surface.

In an operable embodiment, the third hydrophilic material is prepared by using a hydrogel polymer or silicone hydrogel to wrap pigments and form a type of water insoluble pigment particles by way of phase inversion emulsion; and mixing the water insoluble pigment particles and N-vinyl pyrrolidone with pure water to form the third hydrophilic material. The third hydrophilic material after a curing process enables the functional patterned layer to form a decorative pattern capable of changing the color of a user's iris.

In another operable embodiment, the third hydrophilic material is prepared by using ultrasonic liquid-phase dispersion to disperse an electrically conductive material in a solute formed of pure water and alcohol; and the electrically conductive material and the solute being stirred at the same time using ultrasonic oscillation to form a suspension of silver nanoparticles; and lastly, mixing a hydrogel polymer or silicone hydrogel, the suspension of silver nanoparticles and polyvinyl pyrrolidone (PVP) with pure water to form the third hydrophilic material. The third hydrophilic material after a curing process enables the functional patterned layer to form an electrically conductive pattern capable of detecting basal metabolic rate values in a user's tear.

In a further embodiment, the third hydrophilic material is prepared by mixing polyethylene glycol gel (PEG) or silicon dioxide particulates with an ultraviolet (UV) absorbent, medicine, a bioactive agent, an anti-microbial agent, a lubricant, a colorant, an initiator, and a tear stabilizer to form a polymer solution; and then mixing a hydrogel polymer or silicone hydrogel and the polymer solution with pure water to form the third hydrophilic material. The third hydrophilic material after a curing process enables the functional patterned layer to form a polymer pattern capable of preventing eye-related lesions.

In a still further embodiment, the third hydrophilic material is prepared by providing a biomixture composed of live cells, stem cells, exosomes derived from stem cells, proteins, an initiator, or any combination thereof; mixing the biomixture with gel microspheres formed of methacrylate gelatin or polyethylene glycol (PEG) to form a lotion; letting the lotion stand for a predetermined period of time until the lotion is cured to form a biocompatible macromonomer solution; and mixing a hydrogel polymer or silicone hydrogel and the biocompatible macromonomer solution with pure water to form the third hydrophilic material. The third hydrophilic material after a curing process enables the functional patterned layer to form a biocompatible pattern capable of speeding up the regeneration and repair of corneal epithelium, matrix and nerve cells.

In the above four embodiments, the functional patch further includes a secondary functional patterned layer adsorbable to the exposed portions. The secondary functional patterned layer is formed by curing a fourth hydrophilic material, such that an intermolecular force is formed between the secondary functional patterned layer and the functional patterned layer, and the secondary functional patterned layer is detachable from the functional patterned layer. In a preferred embodiment, the functional patterned layer formed of the third hydrophilic material presents a third net-like structure containing a plurality of third pores, and the exposed portions have a fourth hydrophilic material adsorbed thereto to form the secondary functional patterned layer. The secondary functional patterned layer includes secondary permeated portions that permeate into the third pores, and secondary exposed portions that are located on an outer side of the third pores.

The fourth hydrophilic material consists of a resin, a cross-linking agent, an initiator, a solvent, a surfactant or an additive, or any combination thereof, such that the secondary functional patterned layer serves as a protective pattern to protect the functional patterned layer; and the protective pattern presents a fourth net-like structure containing a plurality of fourth pores.

Further, the fourth pores are reducible in size when a type of hydrophilic molecules is added to the fourth hydrophilic material to mix with the resin, the cross-linking agent, the initiator, the solvent, the surfactant or the additive, or any combination thereof.

The present invention is characterized in that the attaching layer of the functional patch is formed of a hydrophilic material different from that for forming the contact lens, so that the attaching layer has relatively closely arranged molecular chain blocks to form net-like structure having only relatively small pores compared to the contact lens. Further, since the pores on the attaching layer are closely arranged, when the molecules of the material for forming the functional patterned layer of the functional patch is coated, pad printed or jet printed on the attaching layer, only a limited part of the material molecules can permeate into the pores of the attaching layer. Thus, the cured functional patterned layer can have a smooth surface without unevenness or damage.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
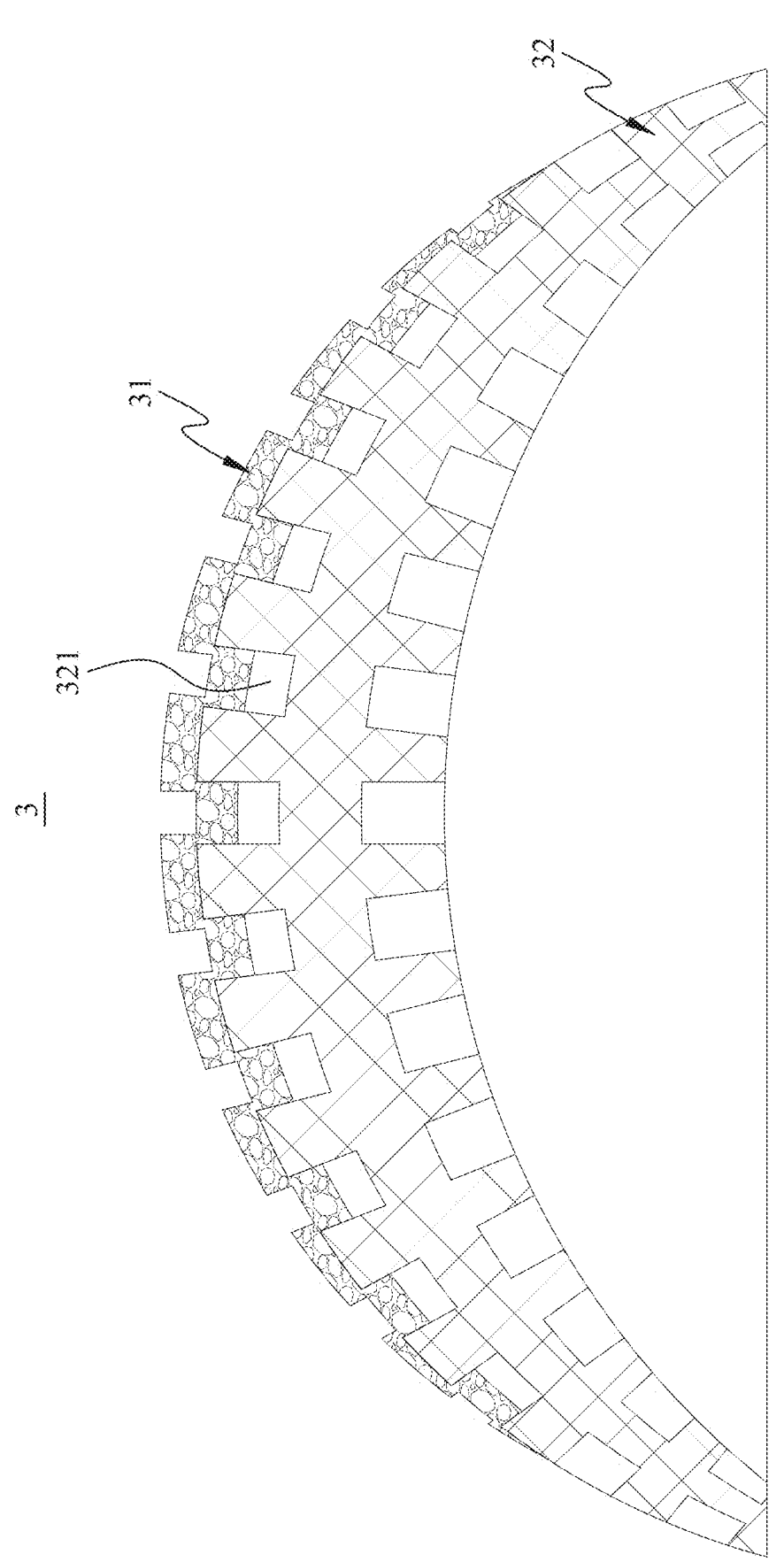
FIG. 1 is a cross sectional view of a conventional colored contact lens.

The present invention will now be described with some preferred embodiments thereof and by referring to the accompanying drawings. For the purpose of easy to understand, elements that are the same in the preferred embodiments are denoted by the same reference numerals.

Figure 2:
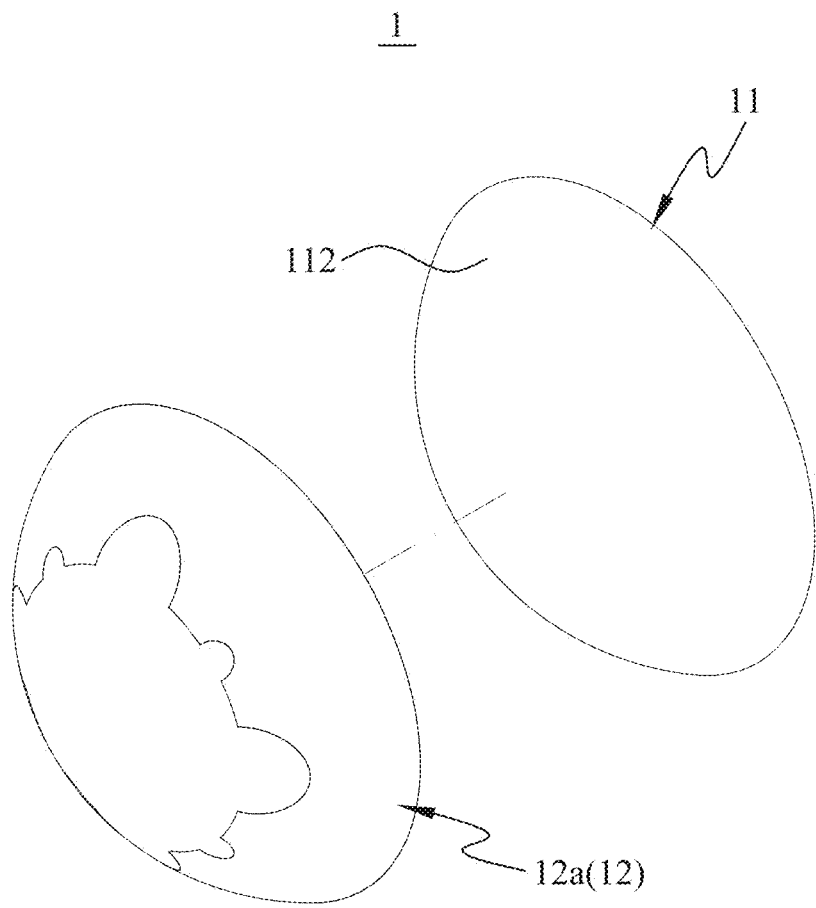
FIG. 2 is an exploded perspective view of a functional patch for use with contact lens according to a first preferred embodiment of the present invention.
Figure 3:
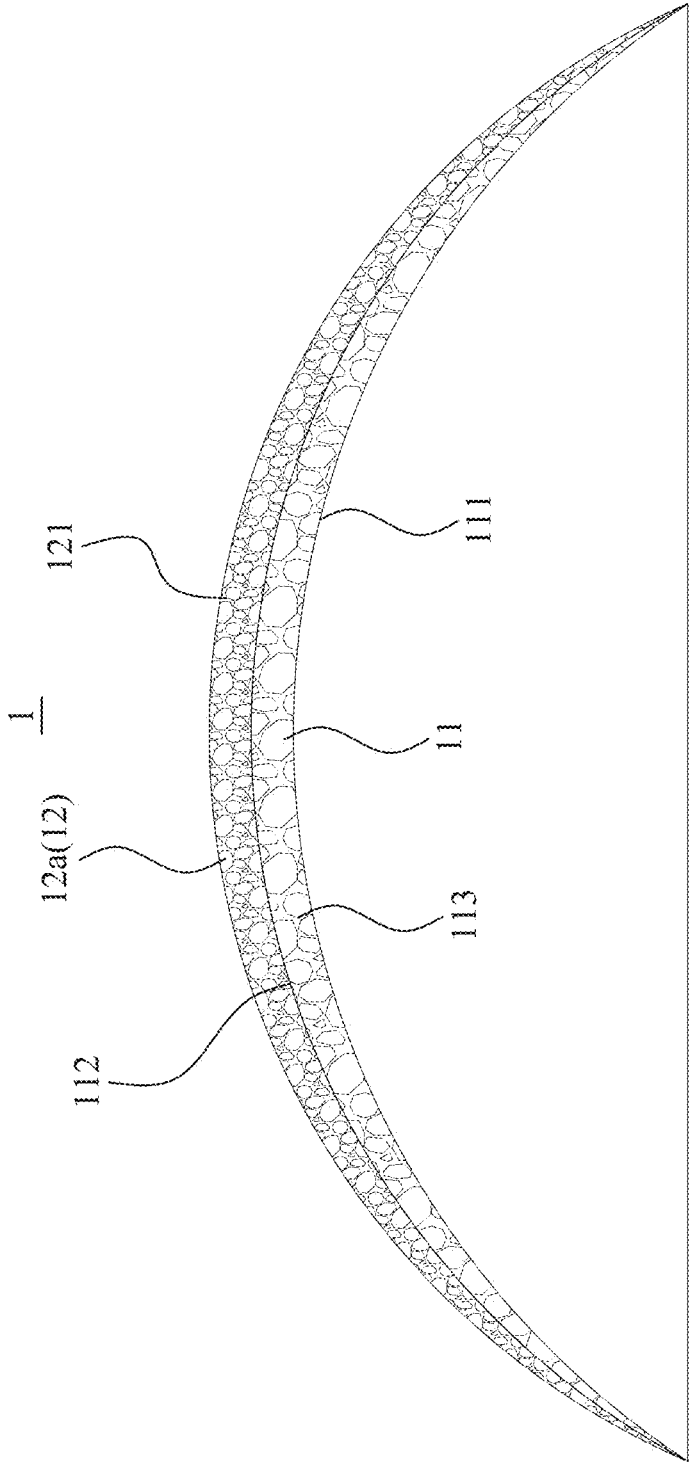
FIG. 3 is a cross sectional view of the functional patch according to the first preferred embodiment of the present invention.
Figure 5A:
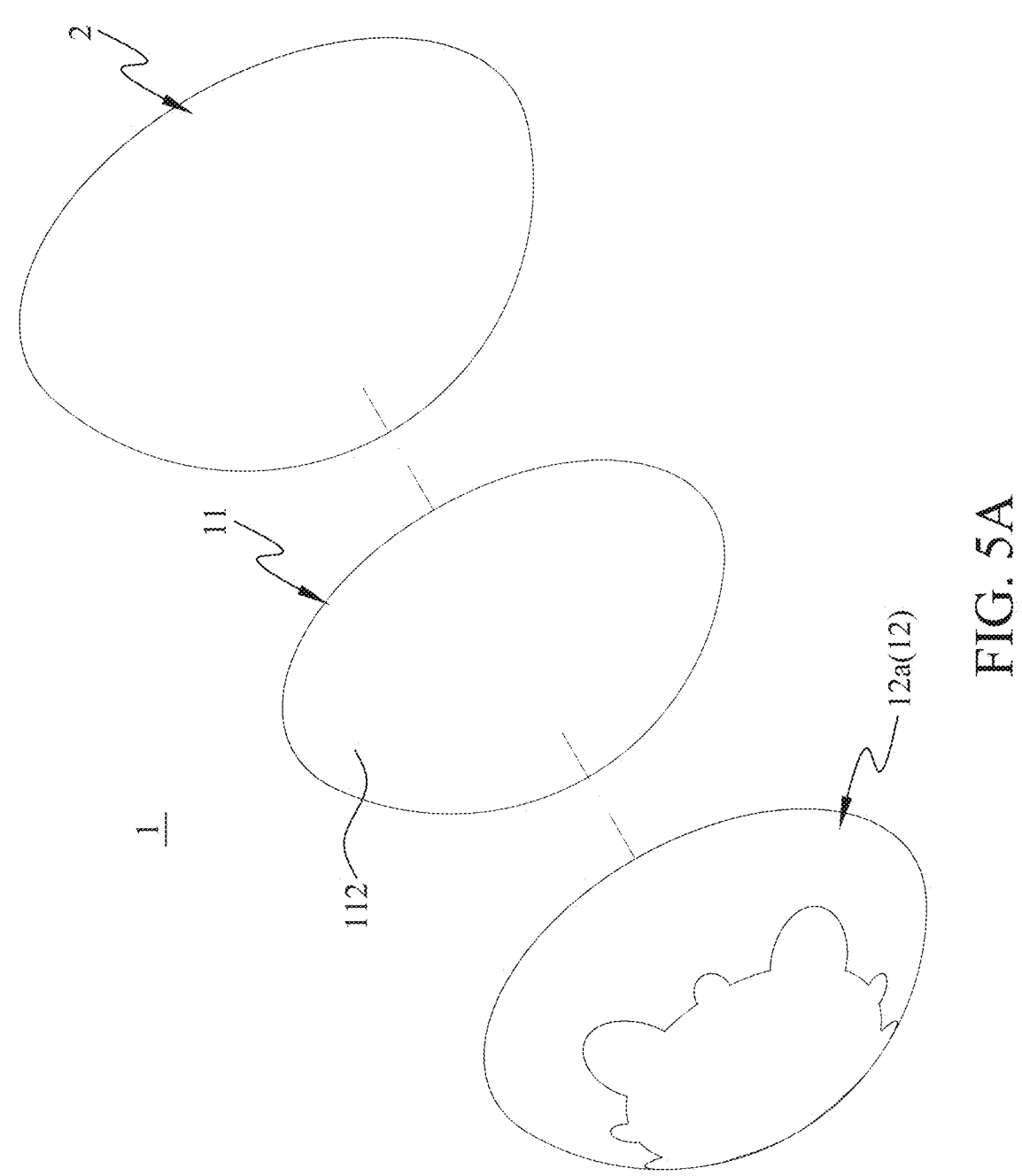
FIG. 5A is an exploded perspective view of the functional patch of FIG. 2 and a contact lens to be used with the functional patch.

Please refer to FIGS. 2 and 3, which are exploded perspective view and assembled cross sectional view, respectively, of a functional patch 1 according to a first preferred embodiment of the present invention for using with a contact lens 2 (see FIG. 5A). The functional patch 1 has a spherical surface with a forward protruded convex central portion, and consists of an attaching layer 11 and a functional patterned layer 12. In the preferred embodiment, the contact lens 2 is made of a first hydrophilic material, which is subjected to a curing process, such that the contact lens 2 has a first net-like structure including a plurality of first pores 21, as shown in FIG. 5C, to facilitate the formation of a desired contact lens profile. In the illustrated first preferred embodiment, the contact lens 2 is manufactured using ethylene glycol dimethacrylate (EGDMA) as a cross-linking agent, so that the first net-like structure presents a smooth surface. The first net-like structure also has the features of being elastic and fast water absorption.

Figure 4:
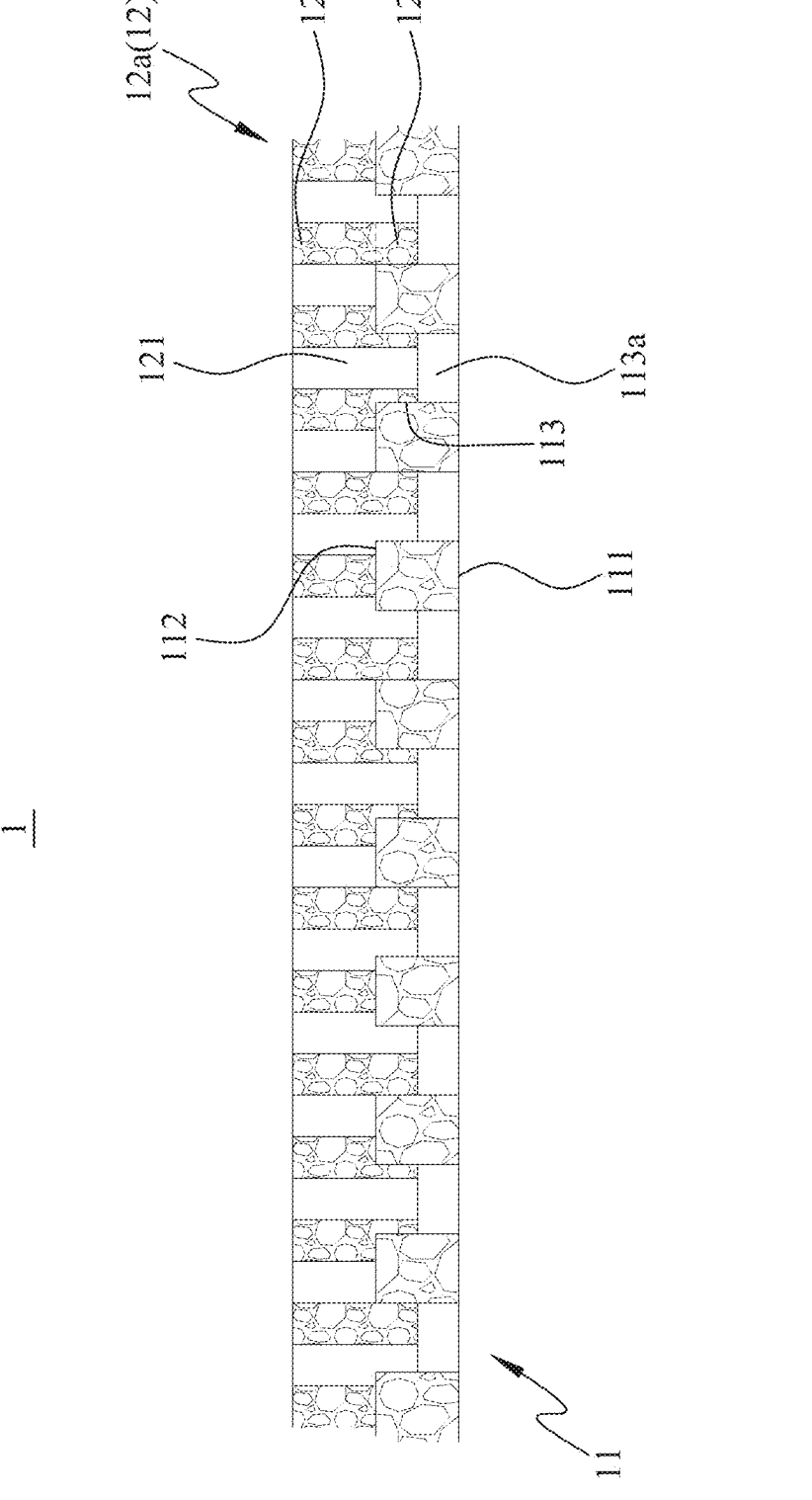
FIG. 4 is a fragmentary, microscopically magnified view of the functional patch according to the first preferred embodiment of the present invention.

As can be seen from FIGS. 2 to 4, the attaching layer 11 is made of a second hydrophilic material different from the first hydrophilic material. Similarly, the second hydrophilic material is subjected to a curing process to facilitate the formation of a desired attaching layer 11 profile, such that the attaching layer 11 presents a second net-like structure.

Two opposite sides of the attaching layer 11 is an attaching surface 111 and a plurality of connecting surfaces 112 spaced on along the attaching surface 111, such that a plurality of second pores 113 is formed between the attaching surface 111 and the connecting surfaces 112. It is noted the second pores 113 have a pore size smaller than that of the first pores 21. In the first preferred embodiment, the second hydrophilic material includes a hydrogel polymer or a silicon hydrogel mixed with a resin, a cross-linking agent, an initiator, an adhesive, a solvent or an additive, or any combination, all of which are different from the material for forming the contact lens 2. The hydrogel polymer can be a polymer consisting of hydrophilic 2-hydroxyethyl methacrylate, N-vinyl pyrrolidone, and methacrylic acid; and the silicone hydrogel is a polymer consisting of highly oxygen permeable silicone hydrogel monomers and polyvinyl pyrrolidone (PVP).

In the first preferred embodiment, the second hydrophilic material is prepared by mixing poly(2-hydroxyethyl methacrylate) (pHEMA) with a dispersant to form a 2-hydroxyethyl methacrylate adhesive; then mixing the 2-hydroxyethyl methacrylate with a cross-linking agent and azobisisobutyronitrile (AIBN) to form a first activating solution; and lastly, mixing the silicone hydrogel, the 2-hydroxyethyl methacrylate adhesive and the first activating solution to form the second hydrophilic material. When the second hydrophilic material is cured, the second net-like structure presented in the attaching layer 11 becomes three-dimensional, such that the second pores 113 have a pore size smaller than that of the first pores 21 of the contact lens 2 and are closely arranged.

Alternatively, the second hydrophilic material may be prepared by mixing pHEMA with a dispersant to form a 2-hydroxyethyl methacrylate adhesive; then mixing the 2-hydroxyethyl methacrylate adhesive with a cross-linking agent and Darocur 1173 photoinitiator to form a second activating solution; and lastly, mixing the silicone hydrogel, the 2-hydroxyethyl methacrylate adhesive and the second activating solution to form the second hydrophilic material. When the second hydrophilic material is cured, the second net-like structure presented in the attaching layer 11 becomes three-dimensional, such that the second pores 113 are closely arranged.

The functional patterned layer 12 is made of a third hydrophilic material different from the second hydrophilic material, such that the functional patterned layer 12 present a third net-like structure containing a plurality of third pores 121. The third hydrophilic material is coated, pad printed, or jet printed on the connecting surface 112 of the attaching layer 11. A part of the third hydrophilic material would permeate into the second pores 113 of the attaching layer 11 to form permeated portions 122, while the remaining part of the third hydrophilic material is cured on the surface of the attaching layer 11 to form exposed portions 123. The permeated portions 122 and the exposed portions 123 together form the functional patterned layer 12. When the permeated portions 122 are located in the second pores 113, they fill only a partial space of the second pores 113, and the remaining space of the second pores 113 are defined as reserved spaces 113a located adjacent to the permeated portions 122. Therefore, the permeated portions 122 are spaced on along the attaching surface 111 of the attaching layer 11. Since the second pores 113 of the attaching layer 11 are closely arranged, only a limited amount of the molecules of the third hydrophilic material is permeated into the second pores 113 of the attaching layer 11. On the other hand, the functional patterned layer 12 has a relatively smooth surface without presenting unevenness that prevents the functional patterned layer 12 from damage. In the first preferred embodiment, the third hydrophilic material is prepared by using a hydrogel polymer or silicone hydrogel to wrap pigments and form a type of water-insoluble pigment particles by way of phase inversion emulsion; and mixing the water insoluble pigment particles and N-vinyl pyrrolidone with pure water to form the third hydrophilic material. When the third hydrophilic material is cured, the functional patterned layer 12 forms a decorative pattern 12a capable of changing the color of a user's iris.

Figure 5B:
FIG. 5B is an assembled cross sectional view of the functional patch and contact lens of FIG. 5A.
Figure 5C:
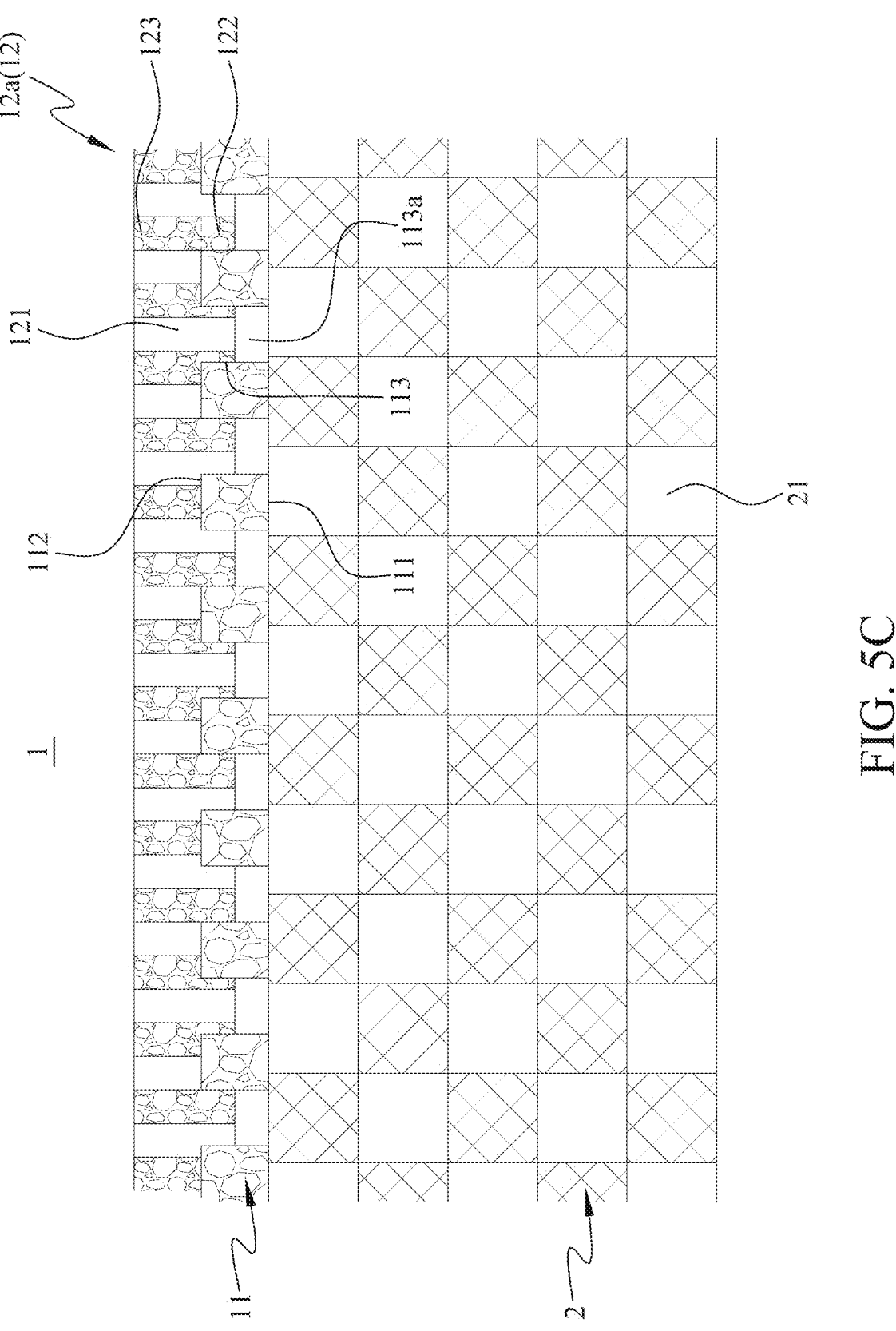
FIG. 5C is a fragmentary, microscopically magnified view of the functional patch and the contact lens of FIG. 5B.

Please refer to FIGS. 5A, 5B and 5C. In the practical use of the functional patch for use with contact lens according to the first preferred embodiment of the present invention, the attaching surface 111 of the attaching layer 11 is in contact with an outer surface of the contact lens 2. Since the contact lens 2 and the attaching layer 11 are made of different first and second hydrophilic material, respectively, there is an intermolecular force between the contact lens 2 and the attaching layer 11, and the first net-like structure of the contact lens 2 can be connected serially to the second net-like structure of the attaching layer 11, such that the attaching layer 11 of the functional patch 1 is, on the one hand, adsorbable to the convex outer surface of the contact lens 2 without being easily stripped therefrom and, on the other hand, is detachable from the convex outer surface of the contact lens 2. When the attaching layer 11 is adsorbed to the contact lens 2, the attaching layer 11 is located between the decorative pattern 12a of the functional patterned layer 12 and the contact lens 2. When the user wears the contact lens 2, an concave inner surface of the contact lens 2 is in contact with the user's cornea, and the decorative pattern 12a of the functional patterned layer 12 is located around the user's iris to change the shape, size, color, and pattern of the user's iris and produces an effect of magnifying the user's eyes.

In an embodiment, the intermolecular force between the attaching layer 11 and the contact lens 2 can be a physical bonding with relatively small bond energy or a chemical bonding with relatively large bond energy. In the case of a physical bonding, it can be a hydrogen bond, a Van der waals force, or a combination thereof. In the case of a chemical bonding, it can be a metal bond, an ion bond, a covalent bond, or any combination thereof.

Figure 5D:
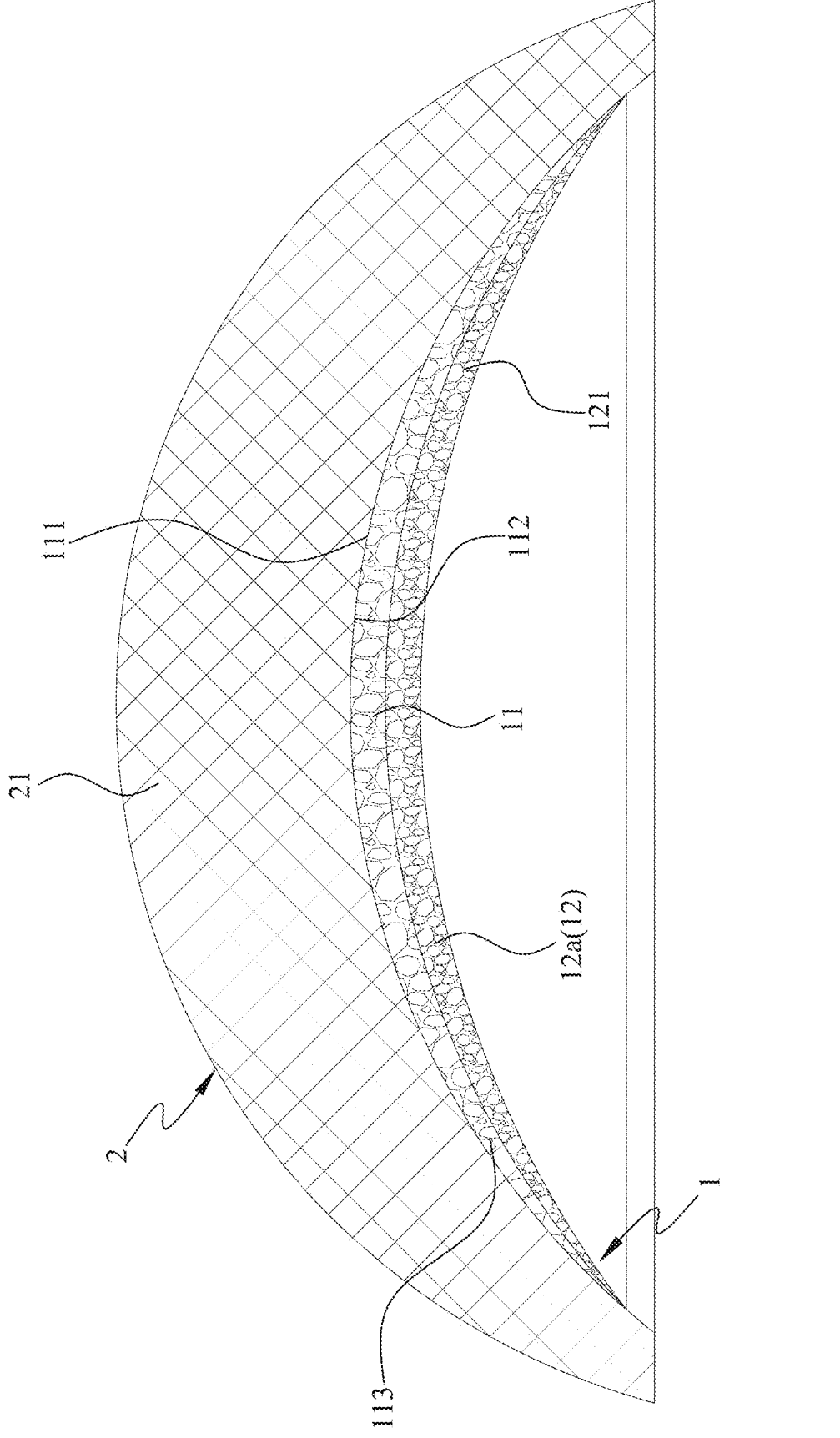
FIG. 5D is a cross sectional view showing an attaching layer of the functional patch is adsorbed to a concave inner surface of the contact lens.

The above description about the adsorption of the attaching layer 11 of the functional patch 1 to the outer convex outer surface of the contact lens 2 is only illustrative. In other embodiments, the attaching layer 11 can also adsorb to the concave inner surface of the contact lens 2, as shown in FIG. 5D. In this case, the functional patterned layer 12 is in contact with the user's cornea when the user wears the contact lens 2.

Figure 6:
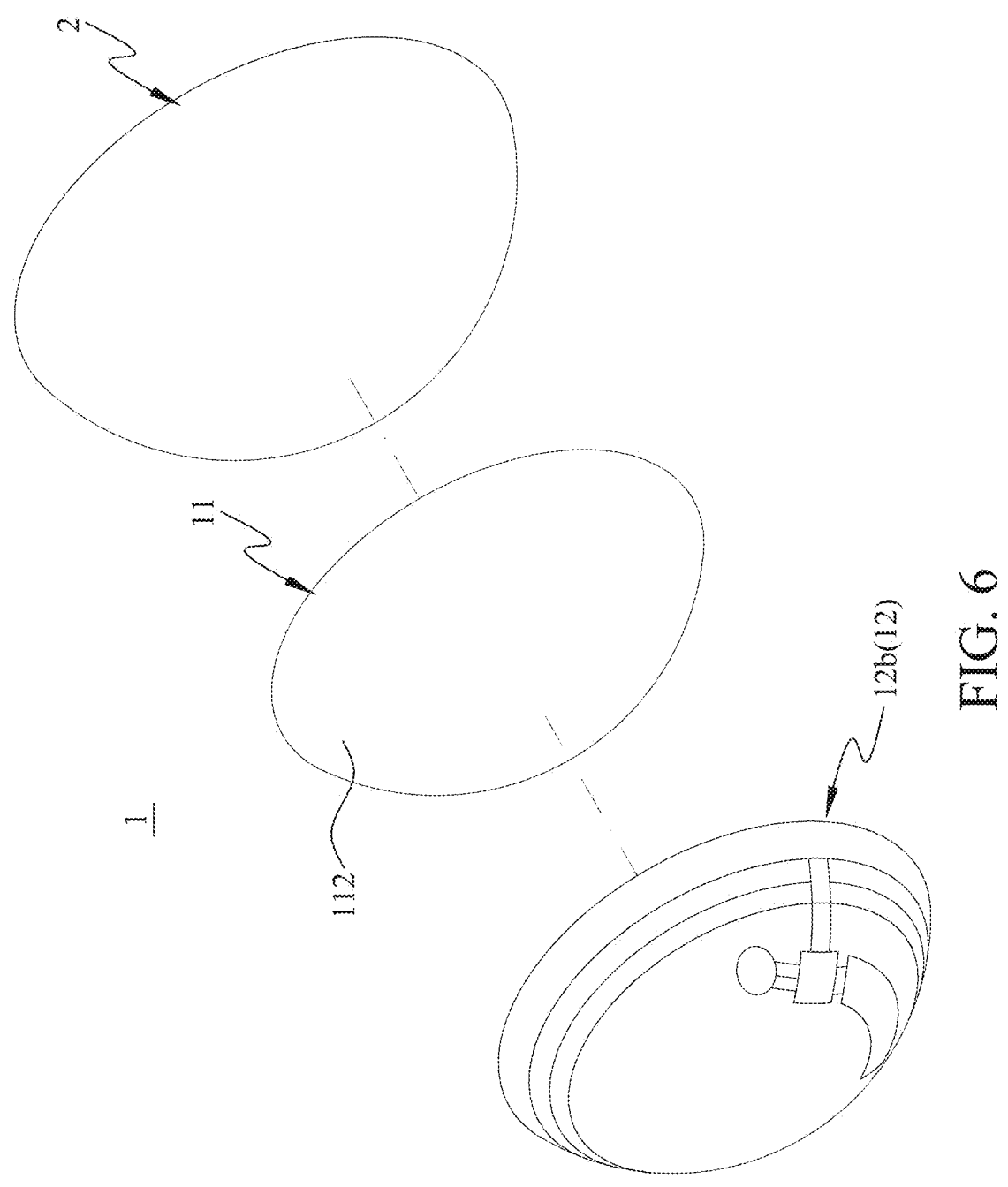
FIG. 6 is an exploded perspective view of a functional patch for use with contact lens according to a second preferred embodiment of the present invention.

Please refer to FIG. 6, which is an exploded perspective view of a functional patch for use with contact lens according to a second preferred embodiment of the present invention. The second preferred embodiment is different from the first one in the composition of the third hydrophilic material. As to the attaching layer 11 and the functional patterned layer 12, since they are structurally the same as those in the first preferred embodiment, they are not repeatedly described herein. In the second preferred embodiment, the third hydrophilic material is prepared by using ultrasonic liquid-phase dispersion to disperse an electrically conductive material in a solute formed of pure water and alcohol; and the electrically conductive material and the solute are stirred at the same time using ultrasonic oscillation to form a suspension of silver nanoparticles; and lastly, a hydrogel polymer or silicone hydrogel, the suspension of silver nanoparticles and polyvinyl pyrrolidone (PVP) are mixed with pure water to form the third hydrophilic material. When the third hydrophilic material prepared in the above steps is cured, the functional patterned layer 12 can form an electrically conductive pattern 12*b* capable of detecting basal metabolic rate values in the user's tear.

As shown in FIG. 6, to use the functional patch of the second preferred embodiment, first attach the attaching layer 11 to the convex outer surface of the contact lens 2, so that the attaching layer 11 is located between the electrically conductive pattern 12*b* of the functional patterned layer 12 and the contact lens 2. That is, when the user wears the contact lens 2, the concave inner surface of the contact lens 2 is in contact with the user's cornea, and the electrically pattern 12*b* of the functional patterned layer 12 is aligned with the user's iris. With this arrangement, the electrically conductive pattern 12*b* is able to detect the basal metabolic rate values in the user's tear, such as glucose, cholesterol, sodium level, potassium level, and electrolyte, and to compute these values to derive detected data and transmit the detected data to an external electronic device. Lastly, the external electronic device interprets the detected data to form relevant information and displays the information on a screen. Thus, the user can have an idea about his or her blood sugar level and do necessary monitoring and controlling of the blood sugar. However, it is understood the description in the second preferred embodiment that the attaching layer 11 is attached to the convex outer surface of the contact lens 2 is only illustrative to facilitate easy explanation of the second embodiment. Just as the first preferred embodiment, the attaching layer 11 in the second preferred embodiment may be otherwise attached to the concave inner surface of the contact lens 2.

Figure 7:
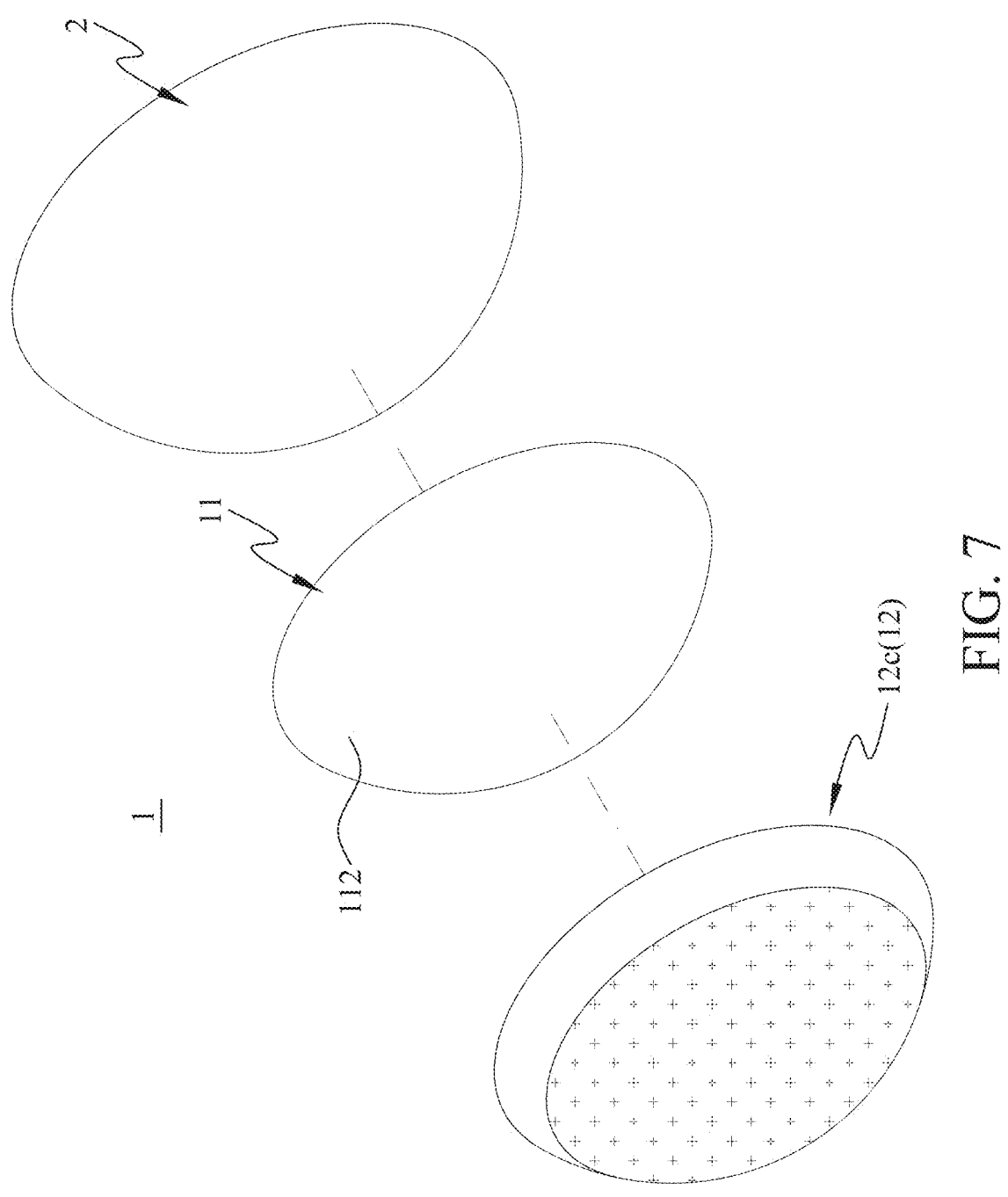
FIG. 7 is an exploded perspective view of a functional patch for use with contact lens according to a third preferred embodiment of the present invention.

Please refer to FIG. 7, which is an exploded perspective view of a third preferred embodiment of the present invention. The third preferred embodiment is different from the first one in the composition of the third hydrophilic material. In the third preferred embodiment, the third hydrophilic material is prepared by mixing polyethylene glycol gel (PEG) or silicon dioxide particulates with an ultraviolet (UV) absorbent, medicine, a bioactive agent, an anti-microbial agent, a lubricant, a colorant, an initiator, and tear stabilizer to form a polymer solution; and then mixing hydrogel polymer or silicone hydrogel and the polymer solution with pure water to form the third hydrophilic material. When the third hydrophilic material prepared in the above steps is cured, the functional patterned layer 12 can form a polymer pattern 12*c* capable of preventing eye-related lesions.

As shown in FIG. 7, to use the functional patch according to the third preferred embodiment, the attaching layer 11 is attached to the contact lens 2 to be located between the polymer pattern 12*c* of the functional patterned layer 12 and the contact lens 2. When the user wears the contact lens 2, the concave inner surface of the contact lens 2 is in contact with the user's cornea, and the polymer pattern 12*c* of the functional patterned layer 12 filters blue light, blocking the blue light from the user's eye to avoid any undesired eye-related lesion. It is also understood the above description in the third preferred embodiment that the attaching layer 11 is attached to the convex outer surface of the contact lens 2 is only illustrative to facilitate easy explanation of the third preferred embodiment. In other operable embodiments, just as in the first preferred embodiment, the attached layer can be otherwise attached to the concave inner surface of the contact lens 2.

Figure 8:
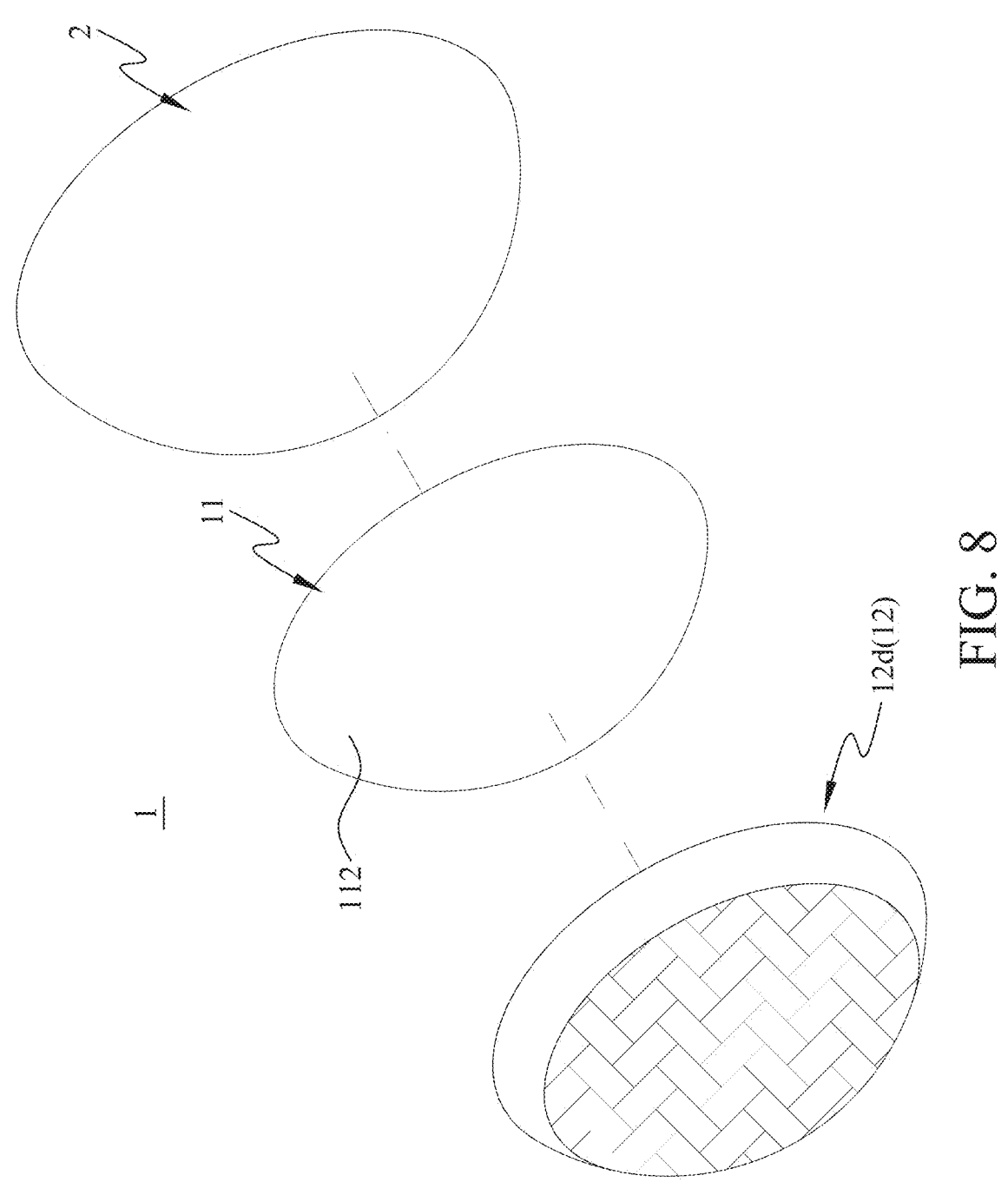
FIG. 8 is an exploded perspective view of a functional patch for use with contact lens according to a fourth preferred embodiment of the present invention.

Please refer to FIG. 8, which is an exploded perspective view of a functional patch for use with contact lens according to a fourth preferred embodiment of the present invention. The fourth preferred embodiment is different from the first one in the composition of the third hydrophilic material. In the fourth preferred embodiment, the third hydrophilic material is prepared by providing a biomixture composed of live cells, stem cells, exosomes derived from stem cells, proteins, an initiator, or a mixture thereof; mixing the biomixture with gel microspheres formed of methacrylate gelatin or polyethylene glycol (PEG) to form a lotion; letting the lotion stand for a predetermined period of time until the lotion is cured to form a biocompatible macromonomer solution; and mixing hydrogel polymer or silicone hydrogel and the biocompatible macromonomer solution with pure water to form the third hydrophilic material. When the third hydrophilic material prepared in the above steps is cured, the functional patterned layer 12 can form a biocompatible pattern 12*d* capable of speeding up the regeneration and repair of corneal epithelium, matrix and nerve cells.

As shown in FIG. 8, to use the functional patch according to the fourth preferred embodiment, first attach the attaching layer 11 to the contact lens 2, so that the attaching layer 11 is located between the biocompatible pattern 12*d* of the functional patterned layer 12 and the contact lens 2. When the user wears the contact lens 2, the concave inner surface of the contact lens 2 is in contact with the user's cornea, and the biocompatible pattern 12*d* of the functional patterned layer 12 can release medicine to treat the user's iris. However, it is understood the description in the fourth preferred embodiment that the attaching layer 12 is attached to the convex outer surface of the contact lens 2 is only illustrative to facilitate explanation the present invention. In other operable embodiments, just as in the first preferred embodiment, the attaching layer 11 may be otherwise attached to the concave inner surface of the contact lens 2.

Figure 9:
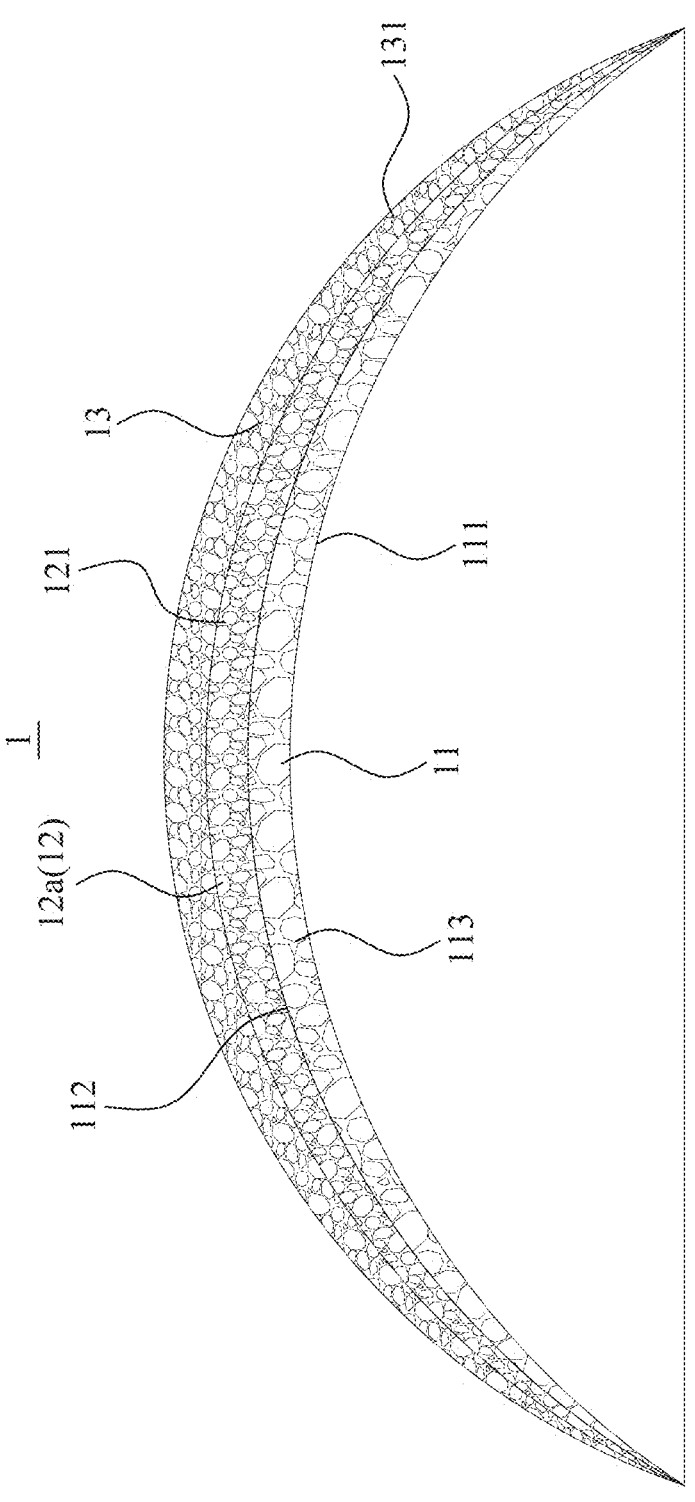
FIG. 9 is an assembled cross sectional view showing a functional patch according to a fifth preferred embodiment of the present invention.

Please refer to FIG. 9, which is an assembled cross sectional view of a functional patch for use with contact lens according to a fifth preferred embodiment of the present invention. In the fifth preferred embodiment, the functional patch 1 further includes a secondary functional patterned layer 13, which is formed of a fourth hydrophilic material different from the first hydrophilic material, such that the secondary functional patterned layer 13 presents a fourth net-like structure containing a plurality of fourth pores 131. Further, the secondary functional patterned layer 13 is subjected a curing process to have a fixed shape or profile. As shown in FIG. 9, the secondary functional patterned layer 13 is connected to the exposed portions 123 of the functional patterned layer 12. Since the functional patterned layer 12 and the secondary functional patterned layer 13 are made of different third and fourth hydrophilic material, respectively, there is an intermolecular force between the functional patterned layer 12 and the secondary functional patterned layer 13. Meanwhile, the third net-like structure of the functional patterned layer 12 is serially connected to the fourth net-like structure of the secondary functional patterned layer 13, such that the secondary functional patterned layer 13, on the one hand, can be adsorbed to the exposed portions 123 of the functional patterned layer 12 without being easily stripped therefrom and, on the other hand, is detachable from the exposed portions 123 of the functional patterned layer 12.

In the fifth preferred embodiment, the fourth hydrophilic material can be the same as the third hydrophilic material used in the first, the second, the third and the fourth preferred embodiment, so that the functional patch 1 can provide two of the four functions of the decorative pattern 12*a*, the electrically conductive pattern 12*b*, the polymer pattern 12*c*, and the biocompatible pattern 12*d* at the same time. Further, the fourth hydrophilic material can be formed of a resin, a cross-linking agent, an initiator, a solvent, a surfactant, an additive, or any combination thereof, such that the secondary functional patterned layer 13 forms a protective pattern to protect the functional patterned layer 12. In the case the secondary functional patterned layer 13 is the protective pattern, the fourth hydrophilic material can further have a type of hydrophilic molecule added thereto, such as polyethylene glycol (PEG). The fourth hydrophilic material containing the polyethylene glycol (PEG) molecules is then further mixed with the resin, the cross-linking agent, the initiator, the solvent, the surfactant, the additive, or any combination thereof to reduce the size of the fourth pores 131.

Figure 10:
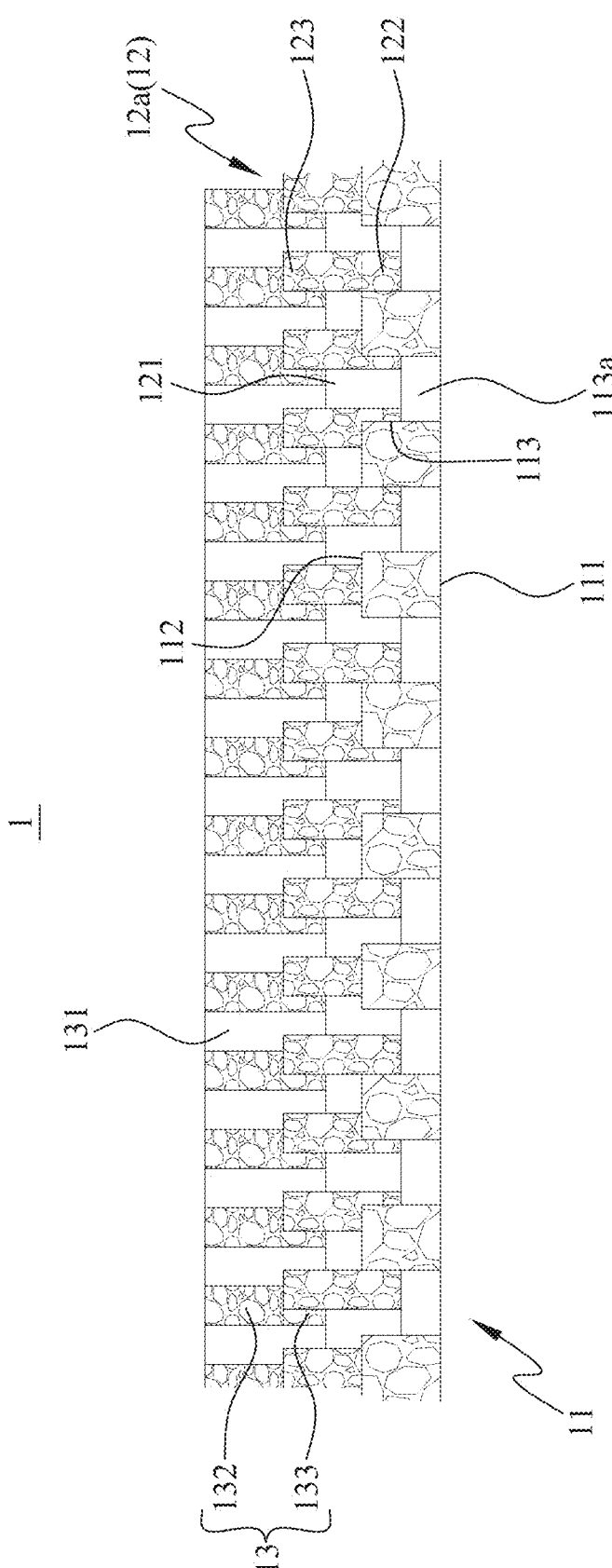
FIG. 10 is a fragmentary, microscopically magnified view of a functional patch according to a sixth preferred embodiment of the present invention.

Please refer to FIG. 10, which is a fragmentary, microscopically magnified view of a functional patch 1 according to a sixth preferred embodiment. The sixth preferred embodiment is different from the fifth one in the way of forming the secondary functional patterned layer 13 on the functional patterned layer 12. In the sixth preferred embodiment, the fourth hydrophilic material is coated, pad printed, or jet printed on the exposed portions 123 of the functional patterned layer 12, such that a part of the fourth hydrophilic material permeates into the third pores 121 of the functional patterned layer 12 to form secondary permeated portions 132, and the remaining part of the fourth hydrophilic material is cured to form secondary exposed portions 133 on the surface of the exposed portions 123. The secondary permeated portions 132 and the secondary exposed portions 133 together form the secondary functional patterned layer 13. With these arrangements, only limited amount of the material molecules of the fourth hydrophilic material can permeate into the third pores 121, allowing the secondary functional patterned layer 13 to have a relatively smooth surface.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A functional patch for use with a contact lens, the contact lens being formed of a first hydrophilic material to present a first net-like structure containing a plurality of first pores, and the functional patch comprising:

an attaching layer formed of a second hydrophilic material different from the first hydrophilic material to present a second net-like structure; the attaching layer presenting the second net-like structure forming an attaching surface adsorbable to the contact lens, a discontinuous connecting surface spaced on along the attaching surface, and a plurality of second pores located between the attaching surface and the connecting surfaces; and the second pores having pore size smaller than that of the first pores; and a third hydrophilic material being provided on the connecting surfaces to form a functional patterned layer; and the functional patterned layer including a permeated portion that permeate into the second pores, and a exposed portion located on an outer side of the connecting surfaces.

2. The functional patch for use with a contact lens as claimed in claim 1, further comprising a secondary functional patterned layer adsorbable to the exposed portions; the secondary functional patterned layer being formed by curing a fourth hydrophilic material, such that there is an intermolecular force between the secondary functional patterned layer and the functional patterned layer, and the secondary functional patterned layer is detachable from the functional patterned layer.

3. The functional patch for use with a contact lens as claimed in claim 2, wherein the fourth hydrophilic material consists of a resin, a cross-linking agent, an initiator, a solvent, a surfactant, an additive, or any combination thereof, such that the secondary functional patterned layer serves as a protective pattern to protect the functional patterned layer; and the protective pattern presenting a fourth net-like structure containing a plurality of fourth pores; and the fourth pores being reducible in size when a type of hydrophilic molecules is further added to the fourth hydrophilic material to mix with the resin, the cross-linking agent, the initiator, the solvent, the surfactant, the additive, or any combination thereof.

4. The functional patch for use with a contact lens as claimed in claim 1, wherein the functional patterned layer formed of the third hydrophilic material presents a third net-like structure containing a plurality of third pores, and a fourth hydrophilic material absorbing the exposed portions to form a secondary functional patterned layer; and the secondary functional patterned layer including secondary permeated portions that permeate into the third pores, and secondary exposed portions that are located on an outer side of the third pores.

5. The functional patch for use with a contact lens as claimed in claim 4, wherein the fourth hydrophilic material consists of a resin, a cross-linking agent, an initiator, a solvent, a surfactant, an additive, or any combination thereof, such that the secondary functional patterned layer serves as a protective pattern to protect the functional patterned layer; and the protective pattern presenting a fourth net-like structure containing a plurality of fourth pores; and the fourth pores being reducible in size when a type of hydrophilic molecules is further added to the fourth hydrophilic material to mix with the resin, the cross-linking agent, the initiator, the solvent, the surfactant, the additive, or any combination thereof.

6. The functional patch for use with a contact lens as claimed in claim 1, wherein the third hydrophilic material is prepared by using a hydrogel polymer or silicone hydrogel to wrap pigments and form a type of water insoluble pigment particles by way of phase inversion emulsion; and mixing the water insoluble pigment particles and N-vinyl pyrrolidone with pure water to form the third hydrophilic material; and the third hydrophilic material after a curing process enabling the functional patterned layer to form a decorative pattern capable of changing the color of a user's iris.

7. The functional patch for use with a contact lens as claimed in claim 1, wherein the third hydrophilic material is prepared by using ultrasonic liquid-phase dispersion to disperse an electrically conductive material in a solute formed of pure water and alcohol; and the electrically conductive material and the solute being stirred at the same time using ultrasonic oscillation to form a suspension of silver nanoparticles; and lastly, mixing a hydrogel polymer or silicone hydrogel, the suspension of silver nanoparticles and polyvinyl pyrrolidone (PVP) with pure water to form the third hydrophilic material; and the third hydrophilic material after a curing process enabling the functional patterned layer to form an electrically conductive pattern capable of detecting basal metabolic rate values in a user's tear.

8. The functional patch for use with a contact lens as claimed in claim 1, wherein the third hydrophilic material is prepared by mixing polyethylene glycol gel (PEG) or silicon dioxide particulates with an ultraviolet (UV) absorbent, medicine, a bioactive agent, an anti-microbial agent, a lubricant, a colorant, an initiator, and a tear stabilizer to form a polymer solution; and then mixing a hydrogel polymer or silicone hydrogel and the polymer solution with pure water to form the third hydrophilic material; and the third hydrophilic material after a curing process enabling the functional patterned layer to form a polymer pattern capable of preventing eye-related lesions.

9. The functional patch for use with a contact lens as claimed in claim 1, wherein the third hydrophilic material is prepared by providing a biomixture composed of live cells, stem cells, exosomes derived from stem cells, proteins, an initiator, or a mixture thereof; mixing the biomixture with gel microspheres formed of methacrylate gelatin or polyethylene glycol (PEG) to form a lotion; letting the lotion stand for a predetermined period of time until the lotion is cured to form a biocompatible macromonomer solution; and mixing a hydrogel polymer or silicone hydrogel and the biocompatible macromonomer solution with pure water to form the third hydrophilic material; and the third hydrophilic material after a curing process enabling the functional patterned layer to form a biocompatible pattern capable of speeding up the regeneration and repair of corneal epithelium, matrix and nerve cells.

* * * * *